United States Patent [19]

Dekker et al.

[11] Patent Number: 4,622,430
[45] Date of Patent: Nov. 11, 1986

[54] DERIVATIVES OF PENTACYCLO UNDECANES, PROCESSES FOR PREPARING THESE COMPOUNDS, AND PHARMACEUTICAL COMPOSITIONS THEREOF

[75] Inventors: Theodor G. Dekker, Pretoria; Douglas W. Oliver, Potchefstroom; Friedrich O. Snyckers; Cornelis J. van der Schyf, both of Pretoria, all of South Africa

[73] Assignee: Noristan Limited, South Africa

[21] Appl. No.: 452,028

[22] Filed: Dec. 21, 1982

[51] Int. Cl.$^4$ .................................. C07C 101/48
[52] U.S. Cl. ........................... 564/458; 568/665; 568/817; 585/22; 570/183; 570/187
[58] Field of Search ............. 564/458; 568/665, 817, 568/; 585/22; 570/183, 187; 514/656, 661, 715, 717, 719, 727, 728, 729, 751, 755, 764, 760

[56] References Cited

U.S. PATENT DOCUMENTS

| 3,449,422 | 6/1969 | Miller | 564/458 |
| 3,456,008 | 7/1969 | Stedman | 564/458 |
| 3,532,741 | 10/1970 | Fukunaga | 564/458 X |
| 3,536,761 | 10/1970 | Hoover et al. | 564/458 X |
| 3,562,317 | 2/1971 | Dunn | 260/514 |
| 3,622,628 | 11/1971 | Stedman | 564/458 |
| 3,641,148 | 2/1972 | Stedman | 564/458 |

FOREIGN PATENT DOCUMENTS 0002896 7/1979 European Pat. Off. .

OTHER PUBLICATIONS

Blum, J., *Tetrahedron Letters*, No. 13, pp. 1117-1120, Pergamon Press, 1975.

*Primary Examiner*—Paul F. Shaver
*Attorney, Agent, or Firm*—Berman, Aisenberg & Platt

[57] ABSTRACT

Pentacyclo[6.3.0.0.$^{2,6}$.0$^{3,10}$.0$^{5,9}$]undecane and its derivatives are prepared. The compounds find use as antiviral agents.

33 Claims, No Drawings

DERIVATIVES OF PENTACYCLO UNDECANES, PROCESSES FOR PREPARING THESE COMPOUNDS, AND PHARMACEUTICAL COMPOSITIONS THEREOF

BACKGROUND OF THE INVENTION

This invention relates to derivatives of pentacyclo undecane, processes for preparing these compounds, and pharmaceutical compositions thereof.

Subsequent to the discovery of the antiviral properties of amantidine, considerable research has taken place in the field of polycyclic compounds. Stedman and others have since 1967 synthesized polycyclic amines having "cage"-type structures, such as the compounds shown in FIG. 1 hereunder, which have shown certain antiviral properties.

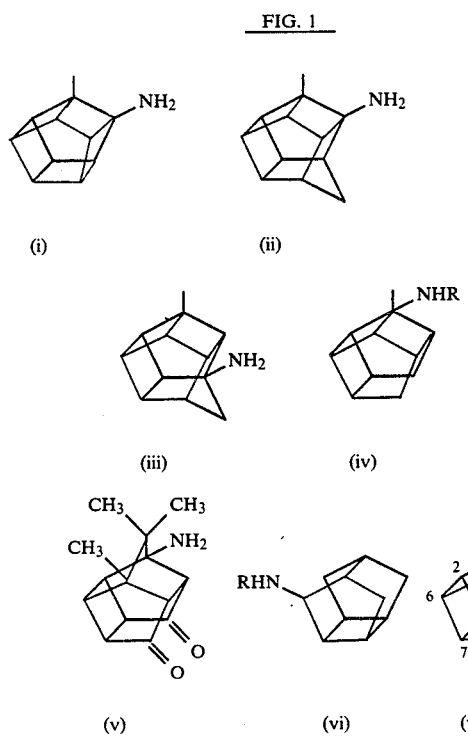

The compounds represented by structural formulae (i), (iv), (v) and (vii) in FIG. 1 have a common pentacyclic framework, namely pentacyclo[5.4.0.0$^{2,6}$.0$^{3,10}$.0$^{5,9}$]undecane, also referred to as pentacyclo[6.3.0.0$^{2,7}$.0$^{4,10}$.0$^{5,9}$]undecane or pentacyclo[6.2.1.0$^{2,7}$.0$^{4,10}$.0$^{5,9}$]undecane or, according to the system used in Chemical Abstracts, as octahydro-1,2,4-ethanylylidene-1H-cyclobuta(cd)pentalene.

U.S. Pat. No. 3,449,422 describes certain pentacyclo undecane amines and their preparation as well as their activity against Asian and swine influenza viruses.

SUMMARY OF THE INVENTION

According to one aspect of the present invention there are provided compounds of the general formula:

$$A-R_1R_2 \qquad (I)$$

wherein A is a substituted or unsubstituted pentacyclo[6.3.0.0$^{2,6}$.0$^{3,10}$.0$^{5,9}$]undecane [commonly known as and hereinafter referred to as (D$_3$)-trishomocubane, and also systematically designated as decahydro-1,3,5-methenocyclopenta(cd)pentalene in Chemical Abstracts], preferably being an alkyl, aryl, a halo, hydroxy, hydroxyalkyl, or amine substituted (D$_3$)-trishomocubane, and R$_1$ and R$_2$ are (either the same or different) hydrogen, an alkyl, aryl, halo, hydroxy, hydroxyalkyl, or amine group, wherein the or each alkyl or aryl group may also have one or more suitable substituents which may be the same or different; and acid-addition salts of such compounds.

In the case that A is a substituted (D$_3$)-trishomocubane, one or more substituents thereon may include an alkyl, aryl, —OR$_3$ group (where R$_3$ includes hydrogen, or an alkyl or aryl group), or a halogen.

According to a preferred aspect of the present invention there are provided compounds of the general formula:

$$A-NHR_1 \qquad (II)$$

wherein A and R$_1$ have the meanings defined above; and acid-addition salts of such compounds.

According to yet another preferred aspect of the present invention there are provided compounds of the general formula:

$$A-NHR_4 \qquad (III)$$

wherein A is an unsubstituted (D$_3$)-trishomocubane, an alky or aryl substituted (D$_3$)-trishomocubane, and R$_4$ is hydrogen, an alkyl, hydroxyalkyl, or aryl group; and acid-addition salts of such compounds.

Preferred types of compounds include the following:

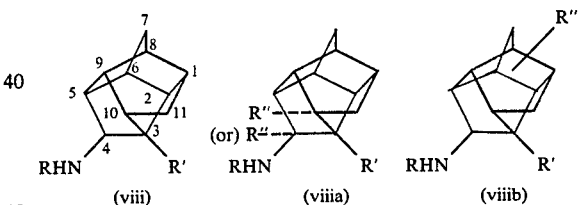

where R, R', and R", which may be the same or different, are as hereinbefore defined (see also hereunder). Each of R' and R" is preferably an alkyl or aryl group.

Particularly preferred compounds include:
4-amino-(D$_3$)-trishomocubane
4-methylamino-(D$_3$)-trishomocubane
4-amino-3-methyl-(D$_3$)-trishomocubane
3-methyl-4-methylamino-(D$_3$)-trishomocubane
4-ethylamino-3-methyl-(D$_3$)-trishomocubane
3-ethyl-4-ethylamino-(D$_3$)-trishomocubane
4-amino-3-phenyl-(D$_3$)-trishomocubane
4-methylamino-3-phenyl-(D$_3$)-trishomocubane
4-ethylamino-3-phenyl-(D$_3$)-trishomocubane
4-butylamino-3-methyl-(D$_3$)-trishomocubane
4-benzylamino-3-methyl-(D$_3$)-trishomocubane
4-($\beta$-phenylethyl)amino-3-methyl-(D$_3$)-trishomocubane
4-amino-3-ethyl-(D$_3$)-trishomocubane The invention extends to stereo-isomers (enantiomers and/or diastereomers) of the previously mentioned compounds. (D$_3$)-trishomocubane, the parent hydrocarbon of the previously mentioned amino compounds, is known to be chiral and therefore has two enantiomeric forms. Any mono-substituted derivative of (D₃)-trishomocubane, for instance compounds with the general structural formula (viii) (when R' is hydrogen) or the monoketone (ix) (when R' is hydrogen) (see below), has two enantiomeric forms. In the case of the 3,4-disubstituted (D₃)-trishomocubane compounds the maximum number of possible stereo-isomers is determined by the state of hybridization of carbon atom number four: if carbon atom number 4 is sp²-hybridized, as is the case with, for instance, the ketone (ix) (when R' is not hydrogen) (see below), then only two isomeric forms (enantiomers) are possible, but if carbon atom number 4 is sp³-hybridized, for instance compounds with the general structural formula (viii) (when R' is not hydrogen), then four isomers are possible i.e. two geometrical isomers, each having two enantiomeric forms. The two compounds generally respond positively to antiviral tests, for example in respect of rabies, and/or exhibit useful anti-Parkinsonistic properties. The known compounds of the type (vii) have also been subjected to anti-Parkinsonistic tests against which they responded positively, although in general to a lesser degree than the compounds of the type (viii).

Also according to the invention, there is provided a first process for preparing compounds of the above general formulae, the process including the steps of converting a parent ketone compound (ix) (see below) to its oxime or to its imine, respectively, according to any known method, followed by reduction thereof to the corresponding amino compound.

corresponding oxime or imine, will, as mentioned above, exist in the form of a racemic mixture, while a pure enantiomer of the substrate ketone, or of the intermediate oxime or imine, will give the corresponding pure enantiomer of (viii) (when R' is hydrogen). Compounds of the type (viii, when R' is not hydrogen, whenever prepared from a racemic mixture of the ketone (ix) (when R' is not hydrogen), or from a racemix mixture of the corresponding intermediate oxime or imine, exist as a mixture of four stereo-isomers, two geometrical isomers, each having two enantiomeric forms. In the case where the amino compound of the type (viii), when R' is not hydrogen, is prepared from a pure enantiomer of the parent ketone (ix) (when R' is not hydrogen), or from a pure enantiomer of the corresponding intermediate oxime or imine, according to this process, a mixture of only two stereo-isomers will be obtained, namely: enantiomeric pure geometrical isomers. It will be understood that one geometrical isomer may predominate, or may even be exclusively formed, depending on the selectivity of the reducing reagent employed for the reduction of the intermediate oxime or imine compound.

Also according to the invention the above said process extends to the preparation of the 8-amino derivatives of pentacyclo[5.4.0.0²,⁶.0³,¹⁰.0⁵,⁹]=undecane, that is compounds of the type (vii), from a parent ketone compound (x), the process including the steps of converting the ketone (x) to its oxime or to its imine, respectively, followed by reduction thereof to the corresponding amino compound (vii), (as illustrated in FIG. 3).

FIG. 3

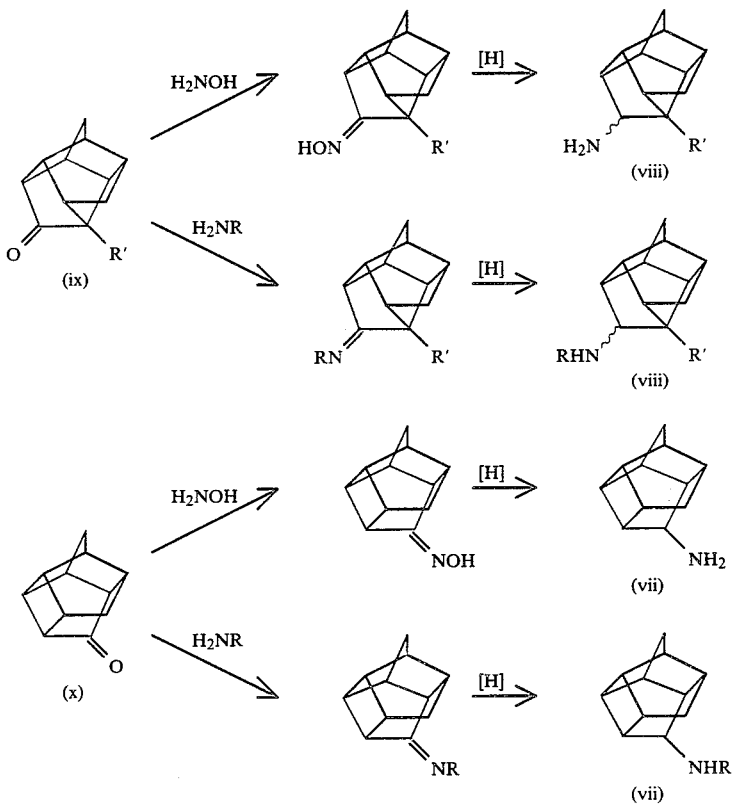

Compounds of the type (viii), when R' is hydrogen, whenever prepared from a racemic mixture of (ix) (when R' is hydrogen), or from a racemic mixture of the The invention thereby provides a new and simplified process for the preparation of compounds of the type (vii), some of which are known compounds.

Due to the molecular shape of the ketone (x), and accordingly of its corresponding oxime and imine, only one geometrical isomer of (vii) is obtained in the latter process, namely the 8-endo amino derivatives of pentacyclo[5.4.0.0$^{2,6}$.0$^{3,10}$.0$^{5,9}$]undecane.

Also according to this invention there is provided a second process for the preparation of compounds of the structural type (viii), when R' is not hydrogen, the process including the steps of converting the tertiary alcohol (xi) (when R' is not hydrogen), which can, for instance, be obtained from a corresponding ketone compound (x) upon treatment thereof with an appropriate Grignard reagent or Grignard type reagent, with an appropriate nitrile (cyanide) in the presence of an acid, preferably concentrated sulphuric acid, to its amide(xii) (when R' is not hydrogen) followed by hydrolysis of the amide (xii) (when R' is not hydrogen) to its corresponding primary amine (viii) (when R is hydrogen and R' is not hydrogen) or followed by reduction of the amide (xii) (when R' is not hydrogen) with an appropriate reducing reagent, for instance lithium aluminium hydride, to its corresponding secondary amine (viii) (when R and R' are not hydrogen). See FIG. 4 hereunder.

case where a racemic mixture of the alcohol (xi) (when R' is not hydrogen) is used as a starting compound, a racemic mixture of only one specific geometrical isomer of the amide (xii) (when R' is not hydrogen) is obtained, while a pure enantiomer of (xi) (when R' is not hydrogen) will give only one specific pure enantiomer of (xii) (when R' is not hydrogen). The stereochemical implications of this rearrangement is illustrated by the stereo drawings used in FIG. 4 for the conversion of a specific enantiomer of (xi) (when R' is not hydrogen) to (xii) (when R' is not hydrogen). The stereochemistry of the amines (viii) (when R is hydrogen and R' is not hydrogen) and (viii) (when R and R' are not hydrogen) is determined by and corresponds to the stereochemistry of the amide (xii) (when R' is not hydrogen).

On the other hand, if a secondary alcohol (xiii) (when R' is hydrogen), which can, for instance, be obtained by reduction of the corresponding ketone compound (x) by any known method, is reacted with an appropriate nitrile (cyanide) in the presence of an acid, preferably concentrated sulphuric acid, the corresponding, unrearranged amide (xiv) is obtained. The amide (xiv) can either be hydrolised to the corresponding primary amine (vii) (when R is hydrogen) or can be reduced with an appropriate reducing agent, such as lithium

FIG. 4.

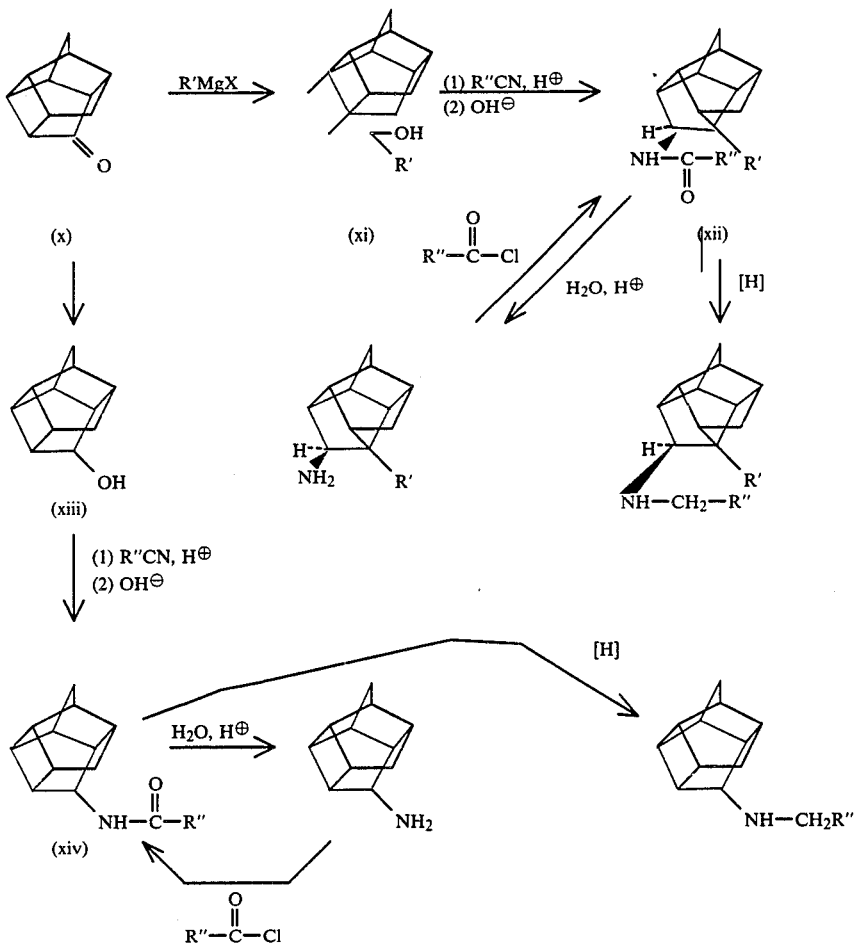

The rearrangement of the alcohol (xi) (when R' is not hydrogen) to the amide (xii) (when R' is not hydrogen) during the second process takes place according to a stereo specific route as is illustrated in FIG. 4: in the aluminium hydride, to the corresponding secondary amine (vii) (when R is not hydrogen), thereby providing yet another novel route for the preparation of amines of the type (vii), with the amino group having the endo configuration.

The amides (xii) and (xiv) can also be obtained by treatment of a corresponding primary amine (viii) or (vii), respectively, with an appropriate acid chloride.

Preferably the first and second processes may include the use of appropriate keto- or hydroxy compounds, either in the form of racemic mixtures or as pure enantiomers, as starting compounds. These ketones or alcohols (i.e. racemic mixtures or pure enantiomers) are either known compounds or may be prepared according to known methods. Geometrical and/or enantiomerical isomers of the compounds of the invention, whenever prepared according to the processes of the invention, may be separated by various methods known in the art of organic chemistry for the separation of geometrical isomers and enantiomers. Furthermore, as outlined above, specific isomers may be obtained directly according to both first and second processes by starting with pure isomers of the substrate ketones, (ix) and (x), respectively. Furthermore, the second process of the invention produces only one specific geometrical isomer of compounds of the type (viii) (when R' is not hydrogen) and therefore the second process may be advantageous over the first process in the case where a specific geometrical isomer is required, thereby limiting the number of isomeric byproducts and also eliminating the subsequent separation of isomers.

Further details of the processes according to the invention will be described in greater detail hereunder.

The invention naturally extends to compounds whenever prepared according to the processes of the invention.

According to a further aspect of the invention there are provided compounds of the aforementioned general formulae when used as antiviral agents, for example in respect of rabies, or when used as anti-Parkinsonistic agents. In other words the invention also extends to at least one compound of the general formulae as defined above, when used for treating viral infections, either therapeutically or prophylactically, more particularly for the treatment of Parkinson's disease for example.

Further according to the invention there are provided pharmaceutical compositions comprising at least one compound of the general formulae as defined above, present in an active amount in admixture with a suitable diluent or adjuvant.

The invention extends to methods of preparing such pharmaceutical compositions, and pharmaceutical compositions whenever prepared by such methods.

DETAILED DESCRIPTION OF THE INVENTION

The invention will now be described in greater detail by means of the following non-limiting examples. These examples illustrate the two basic processes as described hereinbefore for the preparation of the compounds of the type (viii). Certain examples show the preparation of known compounds, namely certain of the compounds of the type (vii), but are included to exemplify the novel processes of the present invention. The processes of the present invention relating to the preparation of compounds of the type (vii) are superior to the prior art process described in U.S. Pat. No. 3,449,422 in respect of simplicity, ease of operation and yield, with a consequent reduction in cost.

The following abbreviations are used:

st=strong;
m=medium;
w=weak;
s=singlet;
bs=braod singlet;
d=doublet;
c=complex;
t=triplet.

In the examples the compound numbers used refer to the compounds listed in Table 3.

EXAMPLE 1

8-endo-amino pentacyclo[$5.4.0.0^{2,6}.0^{3,10}.0^{5,9}$]undecane (1)

To a solution of pentacyclo[$5.4.0.0^{2,6}.0^{3,10}.0^{5,9}$]undecan-8-one (2.1 g) in ethanol (50 ml) was added hydroxylamine hydrochloride (2 g) and a 30% sodium hydroxide solution (20 ml). The mixture was heated under reflux for five hours, cooled and neutralised by bubbling carbon dioxide through the solution. The resultant solution was extracted with dichloro methane and the dichloro methane was removed under reduced pressure. The residue was dissolved in dry tetrahydrofuran (30 ml) and the latter solution was added dropwise over a period of ten minutes to a stirred solution of lithium aluminium hydride (0.5 g) in dry tetrahydrofuran (20 ml). The reaction mixture was refluxed for six hours and cooled. The reaction mixture was then decomposed with aqueous ammonium chloride, diluted with water (200 ml) and extracted with ether. The ether extract was washed twice with water and then extracted with a 5% hydrochloric acid solution. The latter hydrochloric acid solution was washed twice with ether, rendered alkaline with sodium carbonate and extracted with ether. The ether extract was dried over sodium sulphate. To this ether solution was added ether that has been saturated with hydrogen chloride. The precipitated product was collected by filtration. Recrystallisation from ethanol gave colourless crystals.

Elemental analysis of HCl salt: calculated for $C_{11}H_{16}NCl$: C=66.81; H=8.16; N=7.09%. found: C=67.21; H=7.83; N=6.83%.

Mass spectrum: molecular ion at m/e 161.

IR spectrum of free base in $CCl_4$: 2970 (st), 2880 (m), 1675 (w), 1450 (w) and 1275 (w) cm$^{-1}$.

$^1$H NMR spectrum of HCl salt in $D_2O$: δ1.17–1.43 (3H, c with maxima at 1.18; 1.3; 1.37 and 1.42); 1.8 1H, d, J=10.5 Hz), 2.3–2.93 (8H, C) and 3.23 (1H, bs).

$^{13}$C NMR spectrum of HCl salt in $D_2O$: δ57.5; 52.9; 50.6; 49.3; 47.6; 46.8; 46.2; 42.6; 40.8; 40.1; 34.2.

EXAMPLE 2

4-amino-($D_3$)-trishomocubane (11)

The colourless hydrogen chloride salt of this compound was prepared from ($D_3$)-trishomocuban-4-one and recrystallised according to the same procedure as described for the compound in Example 1, except that dry ether was used instead of tetrahydrofuran.

Element analysis of HCl salt: calculated for $C_{11}H_{16}NCl$: C=66.81; H=8.16; N=7.09%. found: C=67.01; H=8.21; N=7.09%.

Mass spectrum: molecular ion at m/e 161.

IR spectrum of free base in $CCl_4$: 2960 (st), 2880 (m), 1450 (w), 1295 (w) and 1100 (w) cm$^{-1}$.

$^1$H NMR spectrum of HCl salt in $D_2O$: δ1.38 (1H, d, J=10.5 Hz), 1.40 (2H, s), 1.57 (1H, d, J=10.5 Hz), 2.18 (7H, bs), 2.43 (1H, bs), 3.50 (1H, s).

EXAMPLE 3

4-amino-3-methyl-(D$_3$)-trishomocubane (22) (mixture of all possible stereo isomers)

The colourless hydrogen chloride salt of this compound was prepared from 3-methyl-(D$_3$)-trishomocuban-4-one and recrystallised according to the same procedure as described for the compound in Example 1.

Elemental analysis of HCl salt: calculated for C$_{12}$H$_{18}$NCl: C=68.07; H=8.57; N=6.61%. found: C=68.51; H=8.75; N=6.45%.

Mass spectrum: molecular ion at m/e 175.

IR spectrum of free base in CCl$_4$: 2960 (st), 2880 (m), 1450 (w) and 1370 (w) cm$^{-1}$.

$^1$H NMR spectrum of HCl salt in D$_2$O: δ1.01 and 1.04 (3H, 2×s); 1.27–1.77 (5H, c with maxima at 1.28; 1.40; 1.48; 1.60; 1.66 and 1.72); 1.93 (1H, bs); 2.16 (4H, bs); 2.47 (1H, bs); 3.27 (1H, bs).

EXAMPLE 4

8-endo-methylamino pentacyclo[5.4.0.0$^{2,6}$.0$^{3,10}$.0$^{5,9}$]undecane (2)

Pentacyclo[5.4.0.0$^{2,6}$.0$^{3,10}$.0$^{5,9}$]undecan-8-one (1 g) was dissolved in absolute alcohol (8 ml) which contained dry methylamine (1.5 g). The solution was sealed in a glass tube and heated for twelve hours at 100° C. The solution was cooled in ice and a solution of sodium boro hydride (2 g) in cold water (20 ml) was added slowly. The solution was then stirred for five hours at room temperature, diluted with water (50 ml) and extracted with ether. The ether solution was washed three times with water and then extracted with a 5% hydrochloric acid solution. The latter hydrochloric acid solution was washed twice with ether, made alkaline with sodium bicarbonate and extracted with ether. The ether extract was dried over sodium sulphate and stripped to dryness. About 25 ml benzene was added to the residue, whereafter it was stripped under reduced pressure. The residue was then redissolved in dry ether.

To this ether solution was added ether that has been saturated with hydrogen chloride. The precipitate was recrystallised from ethanol to give colourless crystals.

Elemental analysis of HCl salt: calculated for C$_{12}$H$_{18}$NCl: C=68.07; H=8.57; N=6.61%. found: C=68.50; H=8.40; H=6.57%.

Mass spectrum: molecular ion at m/e 175.

IR spectrum of free base in CCl$_4$: 2970 (st); 2880 (m); 2860 (m); 2800 (m); 1370 (w) and 1145 (w) cm$^{-1}$.

$^1$H NMR spectrum of HCl salt in D$_2$O: δ1.23 (1H, d, J=10.5 Hz); 1.40 (2H, bs); 1.82 (1H, d, J=10.5 Hz); 2.27–3.13 (12H, c, including s at 2.73 for CH$_3$).

EXAMPLE 5

4-Methylamino-(D$_3$)-trishomocubane (12)

The colourless hydrogen chloride salt of this compound was prepared from (D$_3$)-trishomocuban-4-one and methylamine according to the same procedure as described for the compound in Example 4.

Elemental analysis of HCl salt: calculated for C$_{12}$H$_{18}$NCl: C=68.07; H=8.57; N=6.61%. found: C=68.20; H=8.70; N=6.33%.

Mass spectrum: molecular ion at m/e 175.

IR spectrum of free base in CCl$_4$: 2960 (st); 2880 (m); 2850 (w); 2800 (w); 1470 (w); 1360 (w) and 1130 (w) cm$^{-1}$.

$^1$H NMR spectrum of HCl salt in D$_2$O: δ1.38 (1H, d, J=10.5 Hz); 1.40 (2H, s); 1.60 (1H, d, J=10.5 Hz); 2.0–2.5 (8H, c); 2.73 (3H, s); 3.40 (1H, s).

EXAMPLE 6

3-methyl-4-methylamino-(D$_3$)-trishomocubane (23) (mixture of all possible stereo isomers)

The colourless hydrogen chloride salt of this compound was prepared from 3-methyl-(D$_3$)-trishomocuban-4-one and methylamine according to the same procedure as described for the compound in Example 4.

Elemental analysis of HCl salt: calculated for C$_{13}$H$_{20}$NCl: C=69.16; H=8.93; N=6.20%. found: C=69.40; H=9.10; N=6.15%.

Mass spectrum: Molecular ion at m/e 189.

IR spectrum of free base in CCl$_4$: 2960 (st); 2880 (m); 2860 (m); 2800 (m); 1470 (w); 1450 (d,w) and 1360 (w) cm$^{-1}$.

$^1$H NMR spectrum of HCl salt in D$_2$O: δ1.05 and 1.08 (3H, 2×s); 1.3–1.80 (5H, c, with maxima at 1.32; 1.43; 1.52; 1.63; 1.70; 1.77); 1.98 (1H, bs); 2.23 (4H, bs), 2.47 (1H, bs); 2.77 (3H, s) and 3.23 (1H, s).

EXAMPLE 7

8-endo-(β-hydroxyethyl)amino pentacyclo[5.4.0.0$^{2,6}$.0$^{3,10}$.0$^{5,9}$]undecane (b 4)

The colourless hydrogen chloride salt of this compound was prepared from pentacyclo[5.4.0.0$^{2,6}$.0$^{3,10}$.0$^{5,9}$]undecan-8-one (1 g) and ethanolamine (1.5 g) according to the same procedure as described for the compound in Example 4.

Element analysis of HCl salt: calculated for C$_{13}$H$_{20}$NClO: C=64.58; H=8.34; N=5.79%. found: C=64.32; H=8.21; N=5.62%.

Mass spectrum: molecular ion at m/e 205.

IR spectrum of HCl salt in CHCl$_3$: 3320 (m, broad); 2960 (st); 2870 (m); 1435 (w); 1405 (m); 1260 (w); 1070 (m); 1045 (m) and 1025 (m) cm$^{-1}$.

$^{13}$C NMR spectrum of HCl salt in CDCl$_3$ : δ59.2; 57.3; 50.6; 47.0; 44.4; 41.9 (2×C); 41.0; 39.9; 35.3; 35.1; 34.3; 29.3.

EXAMPLE 8

8-endo-isopropylamino pentacyclo[5.4.0.0$^{2,6}$.0$^{3,10}$.0$^{5,9}$]undecane (5)

The colourless hydrogen chloride salt of this compound was prepared from pentacyclo[5.4.0.0$^{2,6}$.0$^{3,10}$.0$^{5,9}$]undecan-8-one (1 g) and isopropylamine (1.5 g) according to the same procedure as described for the compound in Example 4.

Elemental analysis of HCl salt: calculated for C$_{14}$H$_{22}$NCl: C=70.12; H=9.25; N=5.84%, found: C=69.88; H=9.10; N=5.62%.

Mass spectrum: molecular ion at m/e 203.

IR spectrum of free base (neat): 2965 (st; 2880 (m); 2820 (w); 1460 (w); 1440 (w); 1380 (w); 1330 (w) and 1180 cm$^{-1}$.

$^{13}$C NMR spectrum of HCl salt in CDCl$_3$: δ55.4; 50.8; 46.6; 43.9; 42.5; 41.7; 41.0; 39.5; 36.1; 35.2; 34.0; 29.5; 18.8 (2×C).

EXAMPLE 9

8-endo-butylamino pentacyclo[5.4.0.0$^{2,6}$.0$^{3,10}$.0$^{5,9}$]undecane (6)

The colourless hydrogen chloride salt of this compound was prepared from pentacyclo[5.4.0.0$^{2,6}$.0$^{3,10}$.0$^{5,}$ 9]undecan-8-one (1 g) and butylamine (1.5 g) according to the same procedure as described for the compound in Example 4.

Elemental analysis of HCl salt: calculated for $C_{15}H_{24}NCl$: C=70.98; H=9.53; N=5.52%. found: C=70.91; H=9.69; N=5.21%.

Mass spectrum: molecular ion at m/e 217.

IR spectrum of free base (neat): 2965 (st); 2875 (m); 2805 (w); 1450 (w) and 1140 (w) cm$^{-1}$.

$^{13}$C NMR spectrum of HCl salt in CDCl$_3$: δ58.0; 47.3; 46.8; 44.1; 41.9 (2×C); 41.0; 39.7; 35.4; 35.1; 34.1; 29.3; 27.4; 20.0; 13.3.

EXAMPLE 10

8-endo-isobutylamino pentacyclo[5.4.0.0$^{2,6}$.0$^{3,10}$.0$^{5,9}$]undecane (7)

The colourless hydrogen chloride salt of this compound was prepared from pentacyclo[5.4.0.0$^{2,6}$.0$^{3,10}$.0$^{5,9}$-9]undecan-8-one (1 g) and isobutylamine (3 g) according to the same procedure described for the compound in Example 4.

Elemental analysis of HCl salt: calculated for $C_{15}H_{24}NCl$: C=70.98; H=9.53; N=5.52%. found: C=70.52; H=9.71; N=5.34%.

Mass spectrum: molecular ion at m/e 217.

IR spectrum of free base in CHCl$_3$: 2965 (st); 2870 (w); 1460 (w); 1405 (w); 1325 (w) and 1100 (w) cm$^{-1}$.

$^{13}$C NMR spectrum of HCl salt in CDCl$_3$: δ58.0; 54.2; 46.5; 43.6; 41.5 (2×C); 40.7; 39.3; 34.9; 34.8; 33.8; 29.0; 25.0; 20.4 (2×C).

EXAMPLE 11

8-endo-benzylamino pentacyclo[5.4.0.0$^{2,6}$.0$^{3,10}$.0$^{5,9}$]undecane (9)

(a) The colourless hydrogen chloride salt of this compound was prepared from pentacyclo[5.4.0.0$^{2,6}$.0$^{3,10}$.0$^{5,9}$-9]undecan-8-one (1 g) and benzylamine (0.67 g) according to the same procedure as described for the compound in Example 4.

Elemental analysis of HCl salt:

calculated for $C_{18}H_{22}NCl$: C=75.11; H=7.70; N=4.87%. found: C=74.82; H=7.52; N=4.98%.

Mass spectrum: molecular ion at m/e 251.

IR spectrum of free base in CHCl$_3$: 2965 (st); 2875 (m); 1490 (w); 1450 (m); 1135 (w) and 705 (m) cm$^{-1}$.

$^{13}$C NMR spectrum of HCl salt in CDCL$_3$: δ130.8; 130.0 (2×C); 128.7; 128.6 (2×C); 57.2; 50.8; 46.7; 43.9; 42.3; 41.7; 40.7; 39.6; 35.7; 34.9; 33.9 and 29.4.

(b) A solution of pentacyclo[5.4.0.0$^{2,6}$.0$^{3,10}$.0$^{5,9}$]undecan-8-one (1 g) and benzylamine (0.67 g) was heated on an oil bath for 12 hours at 120° C. The solution was then cooled and diluted with ethanol (8 ml). The reduction of this solution with sodium boro hydride and the isolation of the hydrogen chloride salt, which was identical to the compound prepared in Example 11(a), was done according to the method described in Example 4.

EXAMPLE 12

8-endo-pentylamino pentacyclo[5.4.0.0$^{2,6}$.0$^{3,10}$.0$^{5,9}$]undecane (8)

(a) A solution of pentacyclo[5.4.0.0$^{2,6}$.0$^{3,10}$.0$^{5,9}$]undecan-8-one (1 g) and pentylamine (0.51 g) in dry ethanol (8 ml) was heated in a sealed glass tube for 12 hours at 100° C. The solution was cooled in ice and a solution of sodium boro hydride (2 g) in cold water (20 ml) was added slowly. The solution was then stirred for 5 hours at room temperature, diluted with water (50 ml) and extracted with ether. The ether solution was washed three times with water and then extracted with a 5% hydrochloric acid solution. The latter hydrochloric acid solution was washed twice with ether, made alkaline with sodium carbonate and extracted with ether. The ether extract was dried over sodium sulphate and stripped to dryness. The crystalline residue was recrystallised from petroleum ether to give colourless crystals.

Elemental analysis of free base: calculated for $C_{16}H_{25}N$: C=83.06; H=10.89; N=6.05%. found: C=82.88; H=10.98; N=5.89%.

Mass spectrum: molecular ion at m/e 231.

IR spectrum of free base (neat): 2960 (st); 2950 (st); 2870 (m); 2800 (m); 1450 (m); 1375 (w); 1360 (w); 1350 (w); 1290 (w); 1270 (w); 1180 (w) and 1140 (m) cm$^{-1}$.

$^{13}$C NMR spectrum of free base in CDCl$_3$: δ58.0; 47.4; 46.7; 44.0; 41.8 (2×C); 40.9; 39.6; 35.3; 35.0; 33.9; 29.2; 28.7; 25.0; 21.7 and 13.5.

(b) A solution of pentacyclo[5.4.0.0$^{2,6}$.0$^{3,10}$.0$^{5,9}$ undecan-8-one (1 g) in pentylamine (0.51 g) was heated for 12 hours at 100° C., under reflux conditions. The reaction mixture was cooled and diluted with ethanol (8 ml). The reduction of the latter solution with sodium boro hydride and the isolation of the amine, which was identical to the compound prepared in Example 12(a), was done as described in Example 12(a).

EXAMPLE 13

8-endo-octylamino pentacyclo[5.4.0.0$^{2,6}$.0$^{3,10}$.0$^{5,9}$]undecane (10)

(a) This colourless amine was prepared from pentacyclo[5.4.0.0$^{2,6}$.0$^{3,10}$.0$^{5,9}$]undecan-8-one (1 g) and octylamine (0.80 g) according to the same procedure as described for the compound in Example 12(a).

Elemental analysis of the free base: calculated for $C_{19}H_{31}N$: C=83.45; H=11.42; N=5.12%. found: C=83.01; H=11.60; N=5.01%.

Mass spectrum: molecular ion at m/e 273.

IR spectrum of free base in CHCl$_3$: 2960 (st); 2870 (m); 1590 (w); 1450 (w); 1410 (w); 1225 (w) and 1060 (w) cm$^{-1}$.

$^{13}$C NMR spectrum of free base in CDCl$_3$: δ58.0; 47.5; 46.7; 44.0; 41.9; 41.8; 40.9; 39.6; 35.4; 35.0; 34.0; 31.3; 29.3; 28.7 (2×C); 26.7; 25.4; 22.2 and 13.6.

(b) This amine was also prepared from pentacyclo[5.4.0.0$^{2,6}$.0$^{3,10}$.0$^{5,9}$]undecan-8-one (1 g) and octylamine (0.80 g) according to the same procedure as described in Example 12(b).

EXAMPLE 14

(a) Concentrated sulphuric acid (4,5 ml) was added slowly to a well-stirred ice cold solution of acetonitrile (12 ml). Pentacyclo[5.4.0.0$^{2,6}$.0$^{3,10}$.0$^{5,9}$]undecan-8-endo-ol (0.5 g) was added to the latter cold solution and the reaction mixture was stirred overnight at room temperature. whereafer it was poured onto ice and made alkaline with 10% sodium hydroxide. The precipitated 8-endo-acetamido pentacyclo[5.4.0.0$^{2,6}$.0$^{3,10}$.0$^{5,9}$]undecane was collected by filtration and dried under vacuum.

IR spectrum (KBr-disc): 3320 (st); 2990 (st); 2895 (m); 1650 (st); 1555 (st); 1385 (m); 1315 (w); 1295 (m); 1270 (w); 1145 (w); 1020 (w); 1000 (w) and 710 (w) cm$^{-1}$.

(b) The latter amide (Example 14(a)) (0,3 g) was refluxed in concentrated hydrochloric acid (10 ml) for 3 days. The reaction mixture was then made alkaline with sodium hydroxide and extracted with ether. The ether extract was washed with water and dried over sodium sulphate. Upon bubbling of dry hydrogen chloride through the ether solution the hydrogen chloride salt of 8-endo-amino pentacyclo[5.4.0.0$^{2,6}$.0$^{3,10}$.0$^{5,9}$]undecane (1), which was identical to the product prepared in Example 1, precipitated out.

(c) A solution of 8-endo-acetamido pentacyclo[5.4.0.0$^{2,6}$.0$^{3,10}$.0$^{5,9}$]undecane (0.5 g) in dry ether (20 ml) was added slowly to a well-stirred suspension of lithium aluminium hydride (0.5 g) in dry ether (20 ml). The reaction mixture was stirred under reflux for an additional 3 hours and then carefully decomposed with water. The ether phase was washed with water and dried over sodium sulphate. Dry hydrogen chloride was bubbled through the ether. The precipitated 8-endo-ethylamino pentacyclo[5.4.0.0$^{2,6}$.0$^{3,10}$.0$^{5,9}$]undecane (3) was filtered off and recrystallised from ethanol.

Elemental analysis of HCl salt: calculated for $C_{13}H_{20}NCl$: C=69.16; H32 8.93; N=6.20%. found: C=69.01; H=8.93; N=6.21%.

Mass spectrum: molecular ion at m/e 189.

IR spectrum of free base (neat): 2970 (st); 2880 (m); 2820 (m); 1450 (m); 1440 (m); 1370 (m); 1350 (w); 1300 (w); 1275 (w); 1185 (w); 1145 (m) and 960 (w) cm$^{-1}$.

$^{13}$C NMR spectrum of HCl salt in CDCl$_3$: δ57.8; 46.9; 44.2; 42.7; 42.1; 41.9; 41.0; 39.8; 35.5; 35.2; 34.1; 29.4; 11.0.

(d) The hydrogen chloride salt of 8-endo-ethylamino pentacyclo[5.4.0.0$^{2,6}$.0$^{3,10}$.0$^{5,9}$]undecane (3) was also prepared from pentacyclo[5.4.0.0$^{2,6}$.0$^{3,10}$.0$^{5,9}$]undecan-8-one and ethylamine according to the procedure as described for the compound in Example 4.

EXAMPLE 15

(a) 4-acetamido-3-methyl-(D$_3$)-trishomocubane was prepared from 8-methyl pentacyclo[5.4.0.0$^{2,6}$.0$^{3,10}$.0$^{5,9}$]undecan-8-endo-ol and acetonitrile according to the same procedure as described for 8-endo-acetamido pentacyclo[5.4.0.0$^{2,6}$.0$^{3,10}$.0$^{5,9}$]undecane (Example 14(a)).

IR spectrum (KBr-disc): 3300 (st); 2970 (st); 2880 (m); 1640 (st); 1540 (st); 1460 (w); 1370 (w); 1330 (w); 1295 (w); 1140 (w) and 1130 (w) cm$^{-1}$.

(b) The latter amide (Example 15(a)) was hydrolised to 4-amino-3-methyl-(D$_3$)-trishomocubane (13) (3R4R/3S4S racemic mixture) according to the procedure described in Example 14(b).

Elemental analysis of HCl salt: calculated for $C_{12}H_{18}NCl$: C=68.07; H=8.57; N=6.62%. found: C=68.01; H=8.75; N=6.45%.

Mass spectrum: molecular ion at m/e 175.

$^{13}$C NMR spectrum of HCl salt in CDCl$_3$: δ 60.4; 55.3; 49.4; 48.9; 47.4; 46.6; 46.2; 45.6; 42.0; 33.6; 31.5 and 15.0.

(c) 4-acetamido-3-methyl-(D$_3$)-trishomocubane (Example 15(a)) was reduced with lithium aluminium hydride to 4-ethylamino-3-methyl-(D$_3$)-trishomocubane (14) (3R4R/3S4S racemic mixture) according to the procedure described in Example 14(c).

Elemental analysis of HCl salt: Calculated for $C_{14}H_{22}NCl$: C=70.12; H=9.25; N=5.84%. found: C=69.98; H=9.35; N=5.96%.

Mass spectrum: molecular ion at m/e 203.

IR spectrum of free base (neat): 2960 (st); 2870 (m); 2820 (w); 1640 (w); 1540 (w); 1455 (w); 1440 (w); 1370 (w); 1280 (w); 1135 (m) and 1125 (m) cm$^{-1}$.

$^{13}$C NMR spectrum of HCl salt in CDCl$_3$: δ 65.3; 55.0; 49.3; 47.0; 46.7; 46.4 (2×C); 45.2; 41.5; 41.3; 33.4; 31.0; 15.2 and 10.7.

EXAMPLE 16

(a) 4-acetamido-3-ethyl-(D$_3$)-trishomocubane was prepared from 8-ethyl pentacyclo[5.4.0.0$^{2,6}$.0$^{3,10}$.0$^{5,9}$]undecan-8-endo-ol and acetonitrile according to the same procedure as described for 8-endo-acetamido pentacyclo[5.4.0.0$^{2,6}$.0$^{3,10}$.0$^{5,9}$]undecane (Example 14(a)).

IR spectrum (KBr-disc): 3300 (m); 2970 (st); 2885 (m); 1640 (st); 1540 (st); 1455 (w); 1375 (m); 1285 (m) and 1135 (w) cm$^{-1}$.

(b) The latter amide (Example 16(a)) was hydrolised to 4-amino-3-ethyl-(D$_3$)-trishomocubane (21) (3R4R/3S4S racemic mixture) according to the method described in Example 14(b).

Elemental analysis of HCl salt: calculated for $C_{13}H_{20}NCl$: C=69.16; H=8.93; N=6.20%. found: C=69.32; H=8.82; N=6.10%.

Mass spectrum: molecular ion at m/e 189.

$^{13}$C NMR spectrum of HCl salt in CDCl$_3$: δ 59.8; 56.4; 48.6; 47.0; 46.8; 45.9; 44.5 (2×C); 41.3; 33.2; 30.9; 20.3 and 9.00.

(c) 3-ethyl-4-ethylamino-(D$_3$)-trishomocubane (18) (3R4R/3S4S racemic mixture) was obtained by reduction of 4-acetamido-3-ethyl-(D$_3$)-trishomocubane according to the procedure described in Example 14(c).

IR spectrum of free base (neat): 2965 (st); 2880 (m); 2820 (w); 1450 (m); 1360 (m); 1330 (w); 1275 (w) and 1130 (m) cm$^{-1}$.

$^{13}$C NMR spectrum of the HCl salt in CDCl$_3$: δ 60.9; 59.4; 46.6; 46.5 (2×C); 46.2; 44.2; 44.1; 41.1; 40.5; 32.8; 30.3; 19.6; 10.2 and 8.8.

Elemental analysis of HCl salt: calculated for $C_{15}H_{24}NCl$: C=70.98; H=9.53; N=5.52%. found: C=71.04; H=9.78; N=5.54%

Mass spectrum: molecular ion at m/e 217.

EXAMPLE 17

4-ethylamino-3-methyl-(D$_3$)-trishomocubane (24) (mixture of all possible stereo isomers)

The colourless hydrogen chloride salt of this compound was prepared from 3-methyl-(D$_3$)-trishomocuban-4-one and ethylamine and recrystallised according to the same procedure as described for the compound in Example 4.

Elemental analysis of HCl salt: calculated for $C_{14}H_{22}NCl$: C=70.12; H=9.25; N=5.84%. found: C=70.32; H=9.10; N=5.71%.

Mass spectrum: molecular ion at m/e 203.

$^{13}$C NMR spectrum of HCl salt in CDCl$_3$: δ 66.9; 65.3; 55.0; 54.1; 49.3; 48.9; 47.9; 47.8; 47.0; 46.7 (2×C?); 46.6; 46.4 (2×C); 45.2; 43.6; 43.0; 42.3; 41.5; 41.3; 33.4 (2×C); 31.0 (2×C); 15.3; 15.2 and 10.7 (2×C).

EXAMPLE 18

4-butylamino-3-methyl-(D$_3$)-trishomocubane (15) (3R4R/3S4S racemic mixture)

The colourless hydrogen chloride salt of this compound was prepared from 8-methyl pentacyclo[5.4.0.0$^{2,6}$.0$^{3,10}$.0$^{5,9}$]undecan-8-endo-ol and butyronitrile according to the same procedure as described for 8-endo-ethylamino pentacylo[5.4.0.0$^{2,6}$.0$^{3,10}$.0$^{5,9}$]undecane in Example 14(a) and 13(c).

Elemental analysis of HCl salt: calculated for $C_{16}H_{26}NCl$: C=71.75; H=9.78; N=5.23%. found: C=71.90; H=9.64; N=5.20%.

Mass spectrum: molecular ion at m/e 231.

$^{13}$C NMR spectrum of HCl salt in CDCl$_3$: δ 65.6; 55.1; 49.3; 47.0; 46.9; 46.4 (3×C); 45.3; 41.3; 33.4; 31.0; 26.9; 20.1; 15.3 and 13.3.

EXAMPLE 19

4-Benzylamino-3-methyl-(D$_3$)-trishomocubane (16) (3R4R/3S4S racemic mixture)

The colourless hydrogen chloride salt of this compound was prepared from 8-methyl pentacyclo[5.4.0.0$^{2,6}$.0$^{3,10}$.0$^{5,9}$]undecan-8-endo-ol and benzonitrile according to the same procedure as described for 8-endo-ethylamino pentacyclo[5.4.0.0$^{2,6}$.0$^{3,10}$.0$^{5,9}$]undecane in Example 14(a) and 14(c).

Elemental analysis of HCl salt: calculated for C$_{19}$H$_{24}$NCl: C=75.60; H=8.01; N=4.64%. found: C=75.91; H=7.91; N=4.50%.

Mass spectrum: molecular ion at m/e 265.

$^{13}$C NMR spectrum of HCl salt in CDCl$_3$: δ 130.5; 130.3 (2×C); 128.6 (3×C); 64.2; 55.1; 49.4; 49.0; 47.1; 47.0; 46.4 (2×C); 45.3; 41.3; 33.3; 30.9 and 15.4.

EXAMPLE 20

4-(β-phenyl)ethylamino-3-methyl-(D$_3$)-trishomocubane (17) (3R4R/3S4S racemic mixture)

The colourless hydrogen chloride salt of this compound was prepared from 8-methyl pentacyclo[5.4.0.0$^{2,6}$.0$^{3,10}$.0$^{5,9}$]undecan-8-endo-ol and benzyl cyanide according to the same procedure as described for 8-endo-ethylamino pentacylo[5.4.0.0$^{2,6}$.0$^{3,10}$.0$^{5,9}$]undecane in Example 14(a) and 14(c).

Elemental analysis of HCl salt: calculated for C$_{20}$H$_{26}$NCl: C=76.04; H=8.30; N=4.43%. found: C=76.10; H=8.24; N=4.30%.

Mass spectrum: molecular ion at m/e 279.

$^{13}$C NMR spectrum of HCl salt in CDCl$_3$: δ 137.2; 128.7 (4×C?); 126.8; 66.3; 55.5; 49.6; 48.2; 47.3; 47.1; 46.7; 45.5; 41.6; 36.1; 33.7; 31.9; 31.3 and 15.6.

EXAMPLE 21

(a) 4-Acetamido-3-phenyl-(D$_3$)-trishomocubane was prepared from 8-phenyl pentacyclo[5.4.0.0$^{2,6}$.0$^{3,10}$.0$^{5,9}$]undecan-8-endo-ol and acetonitrile according to the same procedure as described for 8-endo-acetamido pentacyclo[5.4.0.0$^{2,6}$.0$^{3,10}$.0$^{5,9}$]undecane in Example 14(a).

(b) 4-acetamido-3-phenyl-(D$_3$)-trishomocubane was hydrolysed to 4-amino-3-phenyl-(D$_3$)-trishomocubane (19) (3R4R/3S4S racemic mixture) according to the procedure described in Example 14(b).

Elemental analysis of HCl salt: calculated for C$_{17}$H$_{20}$NCl: C=74.57; H=7.36; N=5.12% found: C=74.63; H=7.53; N=5.21%

Mass spectrum: molecular ion at m/e 237.

Infra red spectrum of free base (CHCl$_3$): 3380 (br, w); 2970 (st); 2890 (m); 1595 (w); 1490 (w); 765 (st); 715 (m) and 700 cm$^{-1}$.

(c) 4-Acetamido-3-phenyl-(D$_3$)-trishomocubane (Example 21(a)) was reduced with lithium aluminium hydride to 4-ethylamino-3-phenyl-(D$_3$)-trishomocubane (20)(3R4R/3S4S racemic mixture) according to the procedure described in Example 14(c).

Elemental analysis of HCl salt: calculated for C$_{19}$H$_{24}$NCl: C=75.60; H=8.01; N=4.64%. found: C=75.64; H=8.24; N=4.81%.

Mass spectrum: molecular ion at m/e 265.

$^{13}$C NMR spectrum of HCl salt in CDCl$_3$: δ 137.9; 128.6 (4×C!); 126.8; 66.9; 63.6; 50.3; 49.6; 47.4; 47.0; 46.0; 44.3; 42.0; 40.7; 33.5; 31.3 and 10.6.

EXAMPLE 22

Add a solution of acetyl chloride (0.5 g) in dry ether (20 ml) slowly to a solution of 8-endo-amino pentacyclo[5.4.0.0$^{2,6}$.0$^{3,10}$.0$^{5,9}$]undecane (1) (prepared in Example 1) (1 g) in dry ether (20 ml). Reflux the reaction mixture for additional period of 2 hours. The ether solution was washed with diluted hydrochloric acid, water and a diluted solution of sodium bicarbonate, then dried over sodium sulphate and finally stripped to dryness. The crystalline residue was identical to the compound prepared in Example 14(a), viz. 8-endo-acetaido pentacyclo[5.4.0.0$^{2,6}$.0$^{3,10}$.0$^{5,9}$]undecane.

EXAMPLE 23

Antagonism or Reserpine-Induced Catalepsy in the Mouse

Male CD-1 mice were deprived of food 18 hours prior to the experiment but water was available ad libitum. The test compounds were prepared in 1% tragacanth and administered orally to groups of five mice.

Four hours prior to the administration of drug or vehicle, each mouse received an intraperitoneal dose of 5 mg/kg of reserpine. Forty-five minutes after the administration of the test compounds or vehicle, each mouse was placed with its forepaws on a 5 cm high cork, in order to assess the presence or absence of catalepsy. Mice which remained in this position for 5 minutes were considered cataleptic. The ED$_{50}$ (i.e. the dose of test compound causing a reduction of the catalepsy score to 50% of the control group score) and 95% confidence limits were determined where appropriate.

Each test compound was tested at doses of 100, 30 and 10 mg/kg. A constant dose volume of 10 ml/kg was employed.

The ED$_{50}$ values of six compounds are listed in Table 1.

EXAMPLE 24

Irwin Dose-Range Study/Acute Toxicity in the Mouse

Male CD-1 mice were deprived of food for 18 hours prior to the experiment but water was available ad libitum except during the observation period. The test compounds were prepared in 1% tragacanth and administered orally to groups of four mice.

The test compounds were tested at doses of 1000, 464, 215 and 100 mg/kg; the dose volume remained constant at 10 ml/kg. The animals were also observed daily for seven days post-dose and any mortalities noted. LD$_{50}$ values were estimated using the method of Horn (Biometrics, 12, 311 (1956)).

The LD$_{50}$ values of six compounds are listed in Table 1.

TABLE 1

The ED$_{50}$ values, LD$_{50}$ values and therapeutic index of some of the pentacyclic compounds.

| COMPOUND NUMBER | ED$_{50}$ | LD$_{50}$ | THERAPEUTIC INDEX* |
|---|---|---|---|
| 11 | 139 | 1000 | 7,2 |
| 14 | 10,0 | 315 | 31,5 |
| 16 | 69,1 | >1000 | >14,5 |
| 18 | 17,3 | 462 | 26,7 |
| 19 | 32,2 | 825 | 25,6 |

*Therapeutic Index = LD$_{50}$/ED$_{50}$

EXAMPLE 25

Anti-Oxotremorine Test in the Mouse

Male CD-1 mice were deprived of food for 18 hours prior to the commencement of the experiment but water was available ad libitum. The test compounds were prepared in 1% tragacanth and were administered orally to groups of 10 mice.

The test compounds were tested at doses of 100, 30 and 10 mg/kg and at a constant dose volume of 10 ml/kg. Thirty minutes after administration of test compound, vehicle or reference standard, the mice received an intraperitoneal injection of oxotremorine (0.4 mg/kg). The intensity of salivation and tremor were scored, for all mice on a 0–3 scale, at 10, 20 and 30 minutes post-oxotremorine (see Table 2 for examples).

TABLE 2

Effects of oral administration of some of the pentacyclic compounds on oxotremorine-induced tremor and salivation in the mouse.

| COMPOUND NUMBER | DOSE (mg/kg) | TIME (MINUTES) | EFFECT[a] | p[b] |
|---|---|---|---|---|
| 16 | 10 | 10 | 1,4 ± 0,2 (T) | <0,001 |
| 16 | 10 | 10 | 1,3 ± 0,2 (S) | <0,01 |
| 17 | 100 | 30 | 1,4 ± 0,2 (T) | <0,01 |
| 17 | 100 | 30 | 1,0 ± 0,3 (S) | <0,001 |
| 19 | 30 | 20 | 1,0 ± 0,2 (S) | <0,001 |
| 23 | 100 | 10 | 1,2 ± 0,2 (T) | <0,001 |
| 23 | 30 | 30 | 0,8 ± 0,2 (S) | <0,001 |
| Vehicle | — | 10,20,30 | 2,6 – 2,9 (T) | |
| Vehicle | — | 10,20,30 | 2,7 – 2,9 (S) | |

[a] Mean score (± s.e.) for tremor (T) and salivation (S) at time. All values are means of 10 animals except numbers in parentheses (which indicate the number of surviving animals) and the control group which contained 20 animals.
[b] Statistical significance of difference from the vehicle-treated group using $x^2$ test (2-sided) when comparing the number of animals in the two groups having a score >2.

EXAMPLE 26

Antiviral Tests in the Mouse

Groups of six three weeks old Swiss-Webster mice (sexes mixed, but homogenous with regard to mass, temperament, age, etc.) were inoculated intramuscularly (hind leg) with 0.03 ml of a dilution of CVS strain of rabies virus capable of killing 100% of animals 11–14 days subsequent to inoculation.

Test compounds were administered, i.p., 24 hours post inoculation at dose levels of 46.4, 21.5 and 10 mg/kg to groups of six mice per dose level to one series of mice, and 96 hours post inoculation at the same dose levels to a second series of mice.

Observations with regard to mortalities were made on a twice-daily basis and any deaths noted. These observations were conducted up to and including day 14. The number of deaths per dose level were compared with simultaneously treated control groups injected at the 24 and 96 hours intervals with water for injection.

Mortality/survival parameters were obtained for each group by noting the number of days survived for each mouse in each group (up to a maximum of 14 days) and adding the six values to obtain a survival parameter of a certain value—a high value representing good survival while a low value denotes a high mortality rate.

The following typical results were obtained:

| COMPOUND NUMBER | DOSAGE - TIME POST INOC. | DOSE (mg/kg) | SURVIVAL PARAMETER |
|---|---|---|---|
| 14 | 24 hours | 46,4 | 59 |
|  |  | 21,5 | 74 |
|  |  | 10 | 64 |
|  |  | 0 (control) | 53 |
|  | 96 hours | 46,4 | 51 |
|  |  | 21,5 | 56 |
|  |  | 10 | 65 |
|  |  | 0 (control) | 52 |
| 19 | 24 hours | 46,4 | 66 |
|  |  | 21,5 | 65 |
|  |  | 10 | 66 |
|  |  | 0 (control) | 59 |
|  | 96 hours | 46,4 | 68 |
|  |  | 21,5 | 71 |
|  |  | 10 | 77 |
|  |  | 0 (control) | 61 |

TABLE 3

STRUCTURES, NUMBERS AND NAMES OF THE COMPOUNDS REFERRED TO IN EXAMPLES 1 TO 26

| STRUCTURE | SUBSTITUENTS | COMPOUND NUMBER | COMPOUND NAME |
|---|---|---|---|
| (pentacyclic structure with NHR at position 8) | R = H | 1 | 8-endo-amino pentacyclo[5.4.0.0$^{2,6}$.0$^{3,10}$.0$^{5,9}$]undecane |
| | R = CH$_3$ | 2 | 8-endo-methylamino pentacyclo[5.4.0.0$^{2,6}$.0$^{3,10}$.0$^{5,9}$]undecane |
| | R = C$_2$H$_5$ | 3 | 8-endo-ethylamino-pentacyclo[5.4.0.0$^{2,6}$.0$^{3,10}$.0$^{5,9}$]undecane |
| | R = CH$_2$CH$_2$OH | 4 | 8-endo-($\beta$-hydroxyethyl)amino pentacyclo[5.4.0.0$^{2,6}$.0$^{3,10}$.0$^{5,9}$]undecane |
| | R = CH(CH$_3$)$_2$ | 5 | 8-endo-isopropylamino pentacyclo[5.4.0.0$^{2,6}$.0$^{3,10}$.0$^{5,9}$]undecane |
| | R = C$_4$H$_9$(n) | 6 | 8-endo-butylamino pentacyclo[5.4.0.0$^{2,6}$.0$^{3,10}$.0$^{5,9}$]undecane |
| | R = CH$_2$—CH(CH$_3$)$_2$ | 7 | 8-endo-isobutylamino pentacyclo[5.4.0.0$^{2,6}$.0$^{3,10}$.0$^{5,9}$]undecane |
| | R = C$_5$H$_{11}$(n) | 8 | 8-endo-pentylamino pentacyclo[5.4.0.0$^{2,6}$.0$^{3,10}$.0$^{5,9}$]undecane |
| | R = CH$_2$C$_6$H$_5$ | 9 | 8-endo-benzylamino pentacyclo[5.4.0.0$^{2,6}$.0$^{3,10}$.0$^{5,9}$]undecane |
| | R = C$_8$H$_{17}$(n) | 10 | 8-endo-octylamino pentacyclo[5.4.0.0$^{2,6}$.0$^{3,10}$.0$^{5,9}$]undecane |
| (trishomocubane structure with NHR and R') | R' = R = H | 11 | 4-amino-(D$_3$)-trishomocubane |
| | R' = H<br>R = CH$_3$ | 12 | 4-methylamino-(D$_3$)-trishomocubane |
| | R' = CH$_3$<br>R = H | 13 | 4-amino-3-methyl-(D$_3$)-trishomocubane |
| | R' = CH$_3$<br>R = C$_2$H$_5$ | 14 | 4-ethylamino-3-methyl-(D$_3$)-trishomocubane |
| | R' = CH$_3$<br>R = C$_4$H$_9$(n) | 15 | 4-butylamino-3-methyl-(D$_3$)-trishomocubane |
| | R' = CH$_3$<br>R = CH$_2$C$_6$H$_5$ | 16 | 4-benzylamino-3-methyl-(D$_3$)-trishomocubane |
| | R' = CH$_3$<br>R = CH$_2$CH$_2$C$_6$H$_5$ | 17 | 4-($\beta$-phenylethyl)amino-3-methyl-(D$_3$)-trishomocubane |
| | R' = C$_2$H$_5$<br>R = C$_2$H$_5$ | 18 | 3-ethyl-4-ethylamino-(D$_3$)-trishomocubane |
| | R' = C$_6$H$_5$<br>R = H | 19 | 4-amino-3-phenyl-(D$_3$)-trishomocubane |

TABLE 3-continued
STRUCTURES, NUMBERS AND NAMES OF THE COMPOUNDS REFERRED TO IN EXAMPLES 1 TO 26

| STRUCTURE | SUBSTITUENTS | COMPOUND NUMBER | COMPOUND NAME |
|---|---|---|---|
| 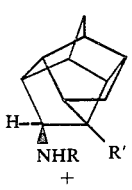 | $R' = C_6H_5$<br>$R = C_2H_5$ | 20 | 4-ethylamino-3-phenyl-$(D_3)$-trishomocubane |
| | $R' = C_2H_5$<br>$R = H$ | 21 | 4-amino-3-ethyl-$(D_3)$-trishomocubane |
| | $R' = CH_3$<br>$R = H$ | 22 | 4-amino-3-methyl-$(D_3)$-trishomocubane |
| | $R' = R = CH_3$ | 23 | 3-methyl-4-methylamino-$(D_3)$-trishomocubane |
| | $R' = CH_3$<br>$R = C_2H_5$ | 24 | 4-ethylamino-3-methyl-$(D_3)$-trishomocubane |

As indicated earlier herein, tests using the aforementioned compounds have shown positive results against rabies and against Parkinson's disease.

It is therefore to be understood that at least some of these compounds can be used in treating a patient for rabies or Parkinson's disease, and consequently pharmaceutical compositions of these compounds form part of the present invention.

In respect of pharmaceutical compositions, one or more of the above suitable compounds may be incorporated in a pharmaceutical composition for administration to a human or animal patient. The method of preparing such composition includes the steps of ensuring that the compound(s) are free of undesirable impurities—this may require repeated re-crystallisation, or washing; comminuting the compound(s) to a required particle size; and incorporating and providing the compound(s) in a desired form together with a suitable adjuvant or diluent for administration to a patient, for example in solid (powder, tablet or capsule form), or liquid form (injectable or liquid medicine) for internal or external application, for example in a suspension or cream for tropical application, or in a (dissolvable) jelly form.

Although the invention in its various aspects has been described above in certain preferred embodiments, it will be readily apparent to any person skilled in the art that various modifications and/or variations of the invention are possible. Such modifications and/or variations of the invention are to be considered as forming part of the invention and as falling within the scope of the appended claims which are also to be considered as part of the disclosure of this invention.

We claim:

1. A compound of one of the formulae:

$$A—R_1R_2 \quad (I)$$

$$A—NHR_1 \quad (II)$$

and $$A—NHR_4 \quad (III)$$

wherein
A is (a) a substituted or unsubstituted $(D_3)$-trishomocubane or (b) an alkyl- or aryl-substituted $(D_3)$-trishomocubane, being (a) for compounds (I) and (III);

$R_1$ is hydrogen, alkyl, aryl, halo, hydroxy, hydroxyalkyl or amino, each alkyl or aryl being optionally substituted by one or more similar or different substituents;

$R_2$ is aryl, amino, alkoxy, aryloxy or hydroxyalkyl, each alkyl or aryl being optionally substituted by one or more similar or different substituents;

$R_4$ is hydrogen (—H), optionally-substituted alkyl or optionally-substituted aryl;

or an acid-addition salt therof.

2. A pharmaceutical composition useful for treating or preventing a viral infection and/or Parkinson's disease which comprises an effective amount of a pharmacologically-acceptable compound in admixture with a suitable diluent or adjuvent; wherein the pharmacologically-acceptable compound is of one of the formulae:

$$A—R_1R_2 \quad (I)$$

$$A—NHR_1 \quad (II)$$

and $$A—NHR_4 \quad (III)$$

wherein
A is (a) a substituted or unsubstituted $(D_3)$-trishomocubane or (b) an alkyl- or aryl-substituted $(D_3)$-trishomocubane, being (a) for compounds (I) and (II);

each of $R_1$ and $R_2$ is, independently, hydrogen, alkyl, aryl, halo, hydroxy, hydroxyalkyl or amino, each alkyl or aryl being optionally substituted by one or more similar or different substitutents;

$R_4$ is hydrogen (—H), optionally-substituted alkyl or optionally-substituted aryl;

or an acid-addition salt thereof.

3. A compound of claim 1 the general formula (II)

$$A—NHR_1 \quad (II)$$

wherein A is a substituted or unsubstituted (D₃)-trishomocubane, and R₁ is hydrogen, an alkyl, aryl, halo, hydroxy, or hydroxylalkyl group, wherein each alkyl or aryl group optionally has one or more suitable substituent(s) which may be the same or different; or an acid addition salt of such compound.

4. A compound as claimed in claim 3, wherein A is a substituted (D₃)-trishomocubane, one or more substituent(s) thereon comprising an alkyl, aryl, —OR₃ group (where R₃ is hydrogen, or an alkyl or aryl group), a halogen, or amine group.

5. A compound of claim 1 the general formula (III)

    (III)

wherein A is an unsubstituted (D₃)-trishomocubane, or an alkyl or aryl substituted (D₃)-trishomocubane, and R₄ is hydrogen, an alkyl, or aryl group, wherein each alkyl and/or aryl group optionally has one or more suitable substituent(s) which may be the same or different; or an acid addition salt of such compound.

6. A compound of claim 1 the structural type

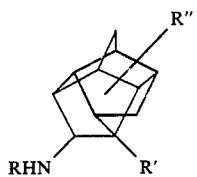    (viiib)

wherein each of R, R', and R" is, independently hydrogen, an alkyl, aryl, halo, hydroxy, or amine group, wherein each alkyl or aryl group optionally has one or more suitable substituent(s) which may be the same or different; or and acid addition salt of such compound.

7. A compound as claimed in claim 6, wherein R is hydrogen or an alkyl group, and each of R' and R" is an alkyl or aryl group.

8. A compound of claim 1 the structural type

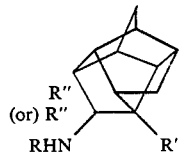    (viiia)

wherein each of R, R', and R" is, independently hydrogen, an alkyl, aryl, halo, hydroxy, or amine group, wherein each alkyl or aryl group optionally has one or more suitable substituent(s) which may be the same or different; or and acid addition salt of such compound.

9. A compound as claimed in claim 8, wherein R is hydrogen or an alkyl group, and each of R' and R" is an alkyl or aryl group.

10. A compound of claim 1 the structural type

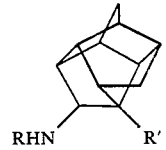    (viii)

wherein each of R and R' is, independently hydrogen, alkyl, aryl, halo, hydroxy, or amine group, wherein each alkyl or aryl group optionally has one or more suitable substituents(s) which may be the same or different; or and acid addition salt of such compound.

11. Compound as claimed in claim 10, wherein R is hydrogen or an alkyl group, and R' is an alkyl or aryl group.

12. The compound of claim 1 4-amino-(D₃)-trishomocubane.

13. The compound of claim 1 4-methylamino-(D₃)-trishomocubane.

14. The compound of claim 1 4-amino-3-methyl-(D₃)-trishomocubane.

15. The compound of claim 1 3-methyl-4-methylamino-(D₃)-trishomocubane.

16. The compound of claim 1 4-ethylamino-3-methyl-(D₃)-trishomocubane.

17. The compound of claim 1 3-ethyl-4-ethylamino-(D₃)-trishomocubane.

18. The compound of claim 1 4-amino-3-phenyl-(D₃)-trishomocubane.

19. The compound of claim 1 4-methylamino-3-phenyl-(D₃)-trishomocubane.

20. The compound of claim 1 4-ethylamino-3-phenyl-(D₃)-trishomocubane.

21. The compound of claim 1 4-butylamino-3-methyl-(D₃)-trishomocubane.

22. The compound of claim 1 4-benzylamino-3-methyl-(D₃)-trishomocubane.

23. The compound of claim 1 4-(β-phenylethyl)amino-3-methyl-(D₃)-trishomocubane.

24. The compound of claim 1 4-amino-3-ethyl-(D₃)-trishomocubane.

25. A compound of claim 1 as claimed in any one of the preceding claims, in the form of a stereo-isomer, either singly or as a mixture of isomers.

26. A compound of claim 1 the general formula (I)

    (I)

wherein A is a substituted or unsubstituted (D₃)-trishomocubane, and R₁ and each of R₂ is, independently, an alkyl, aryl, halo, hydroxy, hydroxyalkyl, or amine group, wherein each alkyl or aryl group optionally has one or more suitable substituents which may be the same or different or R₁ is optionally hydrogen; or an acid addition salt of such compounds.

27. A compound as claimed in claim 26, wherein A is a substituted (D₃)-trishomocubane, one or more substituent(s) thereon comprising an alkyl, aryl, —OR₃ group (where R₃ is hydrogen, or an alkyl or aryl group), a halogen, or amine group.

28. A process for treating or preventing a viral infection and/or Parkinson's disease which comprises administering to a patient afflicted with or subject to viral infection and/or Parkinson's disease an effective amount of a composition as defined in claim 2.

29. A pharmaceutical composition according to claim 2 usefor for treating or preventing a viral infection and which comprises an effective amount of the pharmacologically-acceptable compound in admixture with a suitable diluent or adjuvant.

30. A pharmaceutical composition according to claim 2 useful for treating or preventing Parkinson's disease and which comprises an effective amount of the pharmacologically-acceptable compound in admixture with a suitable diluent or adjuvant.

31. A process for treating or preventing a viral infection which comprises administering to a patient afflicted with or subject to viral infection an effective amount of composition of claim 29.

32. A process for treating or preventing Parkinson's disease which comprises administering to a patient afflicted with or subject to Parkinson's disease an effective amount of composition of claim 30.

33. A compound according to claim 1 which is an amine or substituted amine.

* * * * *